US008172658B2

(12) United States Patent
Svensson (10) Patent No.: US 8,172,658 B2
(45) Date of Patent: May 8, 2012

(54) METHODS, DEVICES, AND COMPUTER PROGRAM PRODUCTS FOR PARTICIPATING IN AN ATHLETIC EVENT WITH A REMOTELY-LOCATED COMPETITOR USING A MOBILE TERMINAL

(75) Inventor: Jan Olof Svensson, Eslov (SE)

(73) Assignee: Sony Ericsson Mobile Communications AB, Lund (SE)

( * ) Notice: Subject to any disclaimer, the term of this patent is extended or adjusted under 35 U.S.C. 154(b) by 1020 days.

(21) Appl. No.: 12/126,330

(22) Filed: May 23, 2008

(65) Prior Publication Data

US 2009/0291726 A1    Nov. 26, 2009

(51) Int. Cl.
  *A63F 13/00* (2006.01)
(52) U.S. Cl. .................. 463/7; 463/36; 463/41; 463/42; 463/43; 702/85; 702/97; 702/127; 702/141; 702/150; 702/155; 702/160; 702/182
(58) Field of Classification Search .......... 702/141–143, 702/85, 97, 127, 150, 155, 158, 160, 182; 463/41–43, 7, 8, 36
See application file for complete search history.

(56) References Cited

U.S. PATENT DOCUMENTS

| 5,980,429 A * | 11/1999 | Nashner ............................ 482/8 |
| 2005/0038626 A1 | 2/2005 | Flentov et al. |
| 2007/0208544 A1 | 9/2007 | Kulach et al. |

FOREIGN PATENT DOCUMENTS

| GB | 2 402 825 A | 12/2004 |
| GB | 2402825 A * | 12/2004 |
| WO | WO 02/30119 A1 | 4/2002 |
| WO | WO 0230119 A1 * | 4/2002 |

OTHER PUBLICATIONS

International Search Report and Written Opinion (17 pages) corresponding to International Application No. PCT/IB2008/055005; Mailing Date: Apr. 3, 2009.
"Sony Ericsson strengthens Cyber-shot™ phone range with two models that take photos further", http://www.sonyericcson.com/cws/corporate/press/pressreleases/pressreleasedetails/c702andc902q1ob.
"Suunto X9M/i", http://www.suuntowatches.com/Suunto-X9Mi.pro, May 18, 2008.
"Polar G3 Stride Sensor Wind—Sensor for RS800)", http://www..polar.fi/en/products/accessories/G3_GPS_sensors_WIND, May 18, 2008.

* cited by examiner

*Primary Examiner* — Sunit Pandya
(74) *Attorney, Agent, or Firm* — Myers Bigel Sibley & Sajovec, P.A.

(57) ABSTRACT

A method of participating in an athletic event with a remotely-located competitor using first and second wireless competition devices includes establishing a wireless communication connection with the second wireless competition device. The second wireless competition device is associated with the remotely-located competitor for the athletic event. Positioning data for the second wireless competition device is received via the wireless communication connection. The positioning data for the second wireless competition device characterizes a previous or real-time performance of the athletic event by the competitor. The received positioning data for the second wireless competition device is provided for display on the first wireless competition device relative to positioning data for the first wireless competition device, which characterizes a performance of the athletic event by a user thereof. Related methods and devices are also discussed.

20 Claims, 5 Drawing Sheets

METHODS, DEVICES, AND COMPUTER PROGRAM PRODUCTS FOR PARTICIPATING IN AN ATHLETIC EVENT WITH A REMOTELY-LOCATED COMPETITOR USING A MOBILE TERMINAL

FIELD OF THE INVENTION

The present invention relates to mobile terminals, and more particularly, to mobile terminals for collecting athletic data and methods of operating the same.

BACKGROUND OF THE INVENTION

Portable electronic devices, such as mobile terminals, increasingly provide a variety of communications, multimedia, and/or data processing capabilities. For example, mobile terminals, such as cellphones and personal digital assistants, may provide access to data in a wide variety of multimedia formats, including text, pictures, music, and/or video.

Conventional mobile terminals often include a Global Positioning System (GPS) receiver that can be used to determine an approximate geographical location of the mobile terminal. In a typical GPS application, the GPS receiver collects and analyzes ranging measurements from signals transmitted by GPS satellites having known locations. More specifically, a constellation of satellites orbiting the earth continually emit a GPS radio signal. A GPS receiver, e.g., a hand-held radio receiver with a GPS processor, receives the radio signals from the closest satellites and measures the time that the radio signal takes to travel from the GPS satellites to the GPS receiver antenna. By multiplying the travel time by the speed of light, the GPS receiver can calculate a range for each satellite in view. Ephemeris information provided in the satellite radio signal typically describes the satellite's orbit and velocity, thereby generally enabling the GPS processor to calculate the position of the GPS receiver through a process of triangulation.

For example, the Garmin Forerunner® is a personal training device that includes a GPS receiver. The GPS receiver may accurately measure athletic performance data including distance, speed, time, altitude, pace, and/or other data that can be important to athletes in training for races. For instance, the Forerunner® can record a user's athletic performance data during a workout and playback the data during a later workout, allowing the user to compete against prior workouts. The Forerunner® also includes wireless heart rate monitor, so that a user can compare his/her pace and heart rate to a past performance over the same run. In addition, the Forerunner® allows a user enter a desired distance, time, and/or pace/speed for a workout, and displays a "Virtual Partner" that runs at the desired pace compared to the user's current pace. Accordingly, conventional mobile terminals including a GPS receiver can be used to accurately track a user's performance during an athletic event.

SUMMARY OF THE INVENTION

According to some embodiments of the present invention, a method of participating in an athletic event with a remotely-located competitor is enabled using first and second wireless competition devices. A wireless communication connection is established with the second wireless competition device, which is associated with the competitor for the athletic event. Positioning data for the second wireless competition device, which characterizes a performance of the athletic event by the competitor, is received via the wireless communication connection. The received positioning data for the second wireless competition device is provided for display on the first wireless competition device relative to positioning data for the first wireless competition device. The positioning data for the first wireless competition device characterizes a performance of the athletic event by a user thereof.

In some embodiments, the received positioning data for the second wireless competition device may be associated with a previous performance of the athletic event by the competitor.

In other embodiments, the received positioning data may be current positioning data for the second wireless competition device received via the wireless communication connection in real-time during the athletic event. In addition, current positioning data for the first wireless competition device may be transmitted to the second wireless competition device via the wireless communication connection in real-time during the athletic event.

In some embodiments, a user selection of a type of athletic event and/or the competitor for the athletic event may be received. The athletic event may be automatically scheduled with the competitor responsive to receiving the user selection.

In other embodiments, automatically scheduling the athletic event may include transmitting an invitation for the athletic event to the second wireless competition device in response to receiving the user selection of the competitor, and receiving an acceptance from the second wireless competition device in response to the invitation. The wireless communication connection may be established with the second wireless competition device prior to a start time for the athletic event in response to receiving the acceptance. Also, a start time for the athletic event may be stored in a calendar application of the first wireless competition device, and an audible, visible, and/or tactile reminder for the athletic event may be provided prior to the start time.

In some embodiments, a user selection of a plurality of competitors may be received, and respective wireless communication connections may be established with a plurality of wireless competition devices associated with respective ones of the plurality of competitors. Respective positioning data for the plurality of wireless competition devices associated with performance of the athletic event by the respective ones of the plurality of competitors may be received via the respective wireless communication connections and displayed on the first wireless competition device relative to the positioning data for the first wireless competition device.

In other embodiments, automatically scheduling the athletic event may include establishing a wireless client-server connection with an athletic competition server in response to receiving the user selection of the type of athletic event. A search request for available competitors for the selected type of athletic event may be transmitted to the athletic competition server via the wireless client-server connection, and search results including the competitor associated with the second wireless competition device may be received from the athletic competition server via the wireless client-server connection in response to the search request. The search results may be displayed on the first wireless competition device, and a user selection of the competitor from the displayed search results may be received. The wireless communication connection may be established with the second wireless competition device prior to a start time for the athletic event in response to receiving the user selection of the competitor from the search results.

In some embodiments, automatically scheduling the athletic event may include receiving a user proposal for the athletic event including a start time and distance for the event. A wireless client-server connection may be established with an athletic competition server in response to receiving the user request, and the proposal may be transmitted to the athletic competition server via the wireless client-server connection. A notification from the athletic competition server may be received when at least the competitor associated with the second wireless competition device has accepted the proposal. The wireless communication connection may be established with the second wireless competition device prior to the start time for the athletic event in response to receiving the notification from the athletic competition server.

In other embodiments, the positioning data for the first wireless competition device may be calculated at a current time after a start time for the athletic event. A current distance traveled by the first wireless competition device may be determined based on the calculated positioning data for the first wireless competition device at the current time. Also, a distance traveled by the second wireless competition device over a time period corresponding to a difference between the start time and the current time may be determined based on the received positioning data for the second wireless competition device. The current distance traveled by the first wireless competition device may be displayed on the first wireless competition device relative to the distance traveled by the second wireless competition device.

In some embodiments, a pace for the first wireless competition device to travel a distance associated with the athletic event before the second wireless competition device may be determined based on the positioning data for the first and second wireless competition devices. The determined pace may be displayed on the first wireless competition device relative to a current pace of the first wireless competition device.

In other embodiments, at least one of the first wireless competition device and the second wireless competition device may be determined to have traveled a distance associated with the athletic event based on the positioning data for the first and second wireless competition devices. As such, at least one of the user and the competitor may be displayed as a winner of the athletic event responsive to determining that the at least one of the first wireless competition device and the second wireless competition device has traveled the distance.

In some embodiments, a level of difficulty for a course traveled by the second wireless competition device during the performance of the athletic event may be determined based on the received positioning data. The display of the received positioning data on the first wireless competition device may be scaled according to the determined level of difficulty.

In other embodiments, establishing the wireless communication connection with the second wireless competition device may include establishing a wireless client-server connection with an athletic competition server that is configured to wirelessly communicate with the second wireless competition device. The positioning for the second wireless competition device may be received from the athletic competition server via the wireless client-server connection, and the received positioning data for the second wireless competition device may be displayed on the first wireless competition device relative to the positioning data for the first wireless competition device.

In some embodiments, the athletic competition server may be further configured to wirelessly communicate with a plurality of wireless competition devices associated with respective competitors for the athletic event. Respective positioning data for the plurality of wireless competition devices may be received from the athletic competition server via the wireless client-server connection. The respective positioning data may characterize respective performances of the athletic event by the respective competitors, and may be displayed on the first wireless competition device relative to the positioning data for the first wireless competition device.

In other embodiments, establishing the wireless communication connection may include establishing a first wireless communication connection between the first wireless competition device and an athletic competition server, and establishing a second wireless communication connection between the second wireless competition device and the athletic competition server. The positioning data may be received from the second wireless competition device via the second wireless communication connection, and may be transmitted to the first wireless competition device via the first wireless communication connection.

In some embodiments, the received positioning data may characterize the performance of a running, bicycling, skiing, and/or skating event by the competitor.

According to further embodiments of the present invention, a first wireless competition device includes a transceiver configured to establish a wireless communication connection with a second wireless competition device. The second wireless competition device is associated with a remotely-located competitor for an athletic event. The first wireless competition device further includes a controller coupled to the transceiver and configured to receive positioning data for the second wireless competition device via the wireless communication connection. The received positioning data for the second wireless competition device characterizes a performance of the athletic event by the competitor. The first wireless competition device also includes a display coupled to the controller and configured to display the received positioning data for the second wireless competition device relative to positioning data for the first wireless competition device. The positioning data for the first wireless competition device characterizes a performance of the athletic event by a user thereof.

In some embodiments, the first wireless competition device may further include a positioning module coupled to the controller. The positioning module may be configured to calculate the positioning data for the first wireless competition device at a current time after a start time for the athletic event. The controller may be configured to determine a current distance traveled by the first wireless competition device based on the calculated positioning data for the first wireless competition device at the current time. The controller may be further configured to determine a distance traveled by the second wireless competition device over a time period corresponding to a difference between the start time and the current time based on the received positioning data for the second wireless competition device. The display may be configured to display the current distance traveled by the first wireless competition device relative to the distance traveled by the second wireless competition device.

According to still further embodiments of the present invention, an athletic competition server includes a transceiver configured to establish a wireless communication collection with a first wireless competition device associated with a remotely-located competitor for an athletic event. The athletic competition server further includes a processor coupled to the transceiver and configured to receive positioning data for the first wireless competition device via the wireless communication connection. The received positioning data for the first wireless competition device characterizes a performance of the athletic event by the competitor. The transceiver is configured to provide the received positioning data for the first wireless competition device for display on a second wireless competition device relative to positioning data for the second wireless competition device. The positioning data for the second wireless competition device characterizes a performance of the athletic event by a user thereof.

Although described above primarily with respect to method and device aspects of the present invention, it will be understood that the present invention may be embodied as methods, devices, and/or computer program products.

DETAILED DESCRIPTION OF EMBODIMENTS OF THE INVENTION

The present invention now will be described more fully hereinafter with reference to the accompanying drawings, in which illustrated embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

The terminology used herein is for the purpose of describing particular embodiments only and is not intended to be limiting of the invention. As used herein, the singular forms "a," "an," and "the" are intended to include the plural forms as well, unless expressly stated otherwise. It should be further understood that the terms "comprises" and/or "comprising" when used in this specification is taken to specify the presence of stated features, integers, steps, operations, elements, and/or components, but does not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. In contrast, when an element is referred to as being "directly coupled" or "directly connected" to another element, there are no intervening elements present. Furthermore, "connected" or "coupled" as used herein may include wirelessly connected or coupled. As used herein, the term "and/or" includes any and all combinations of one or more of the associated listed items, and may be abbreviated as "/".

It will also be understood that, although the terms first, second, etc. may be used herein to describe various elements, these elements should not be limited by these terms. These terms are only used to distinguish one element from another. For example, a first mobile terminal could be termed a second mobile terminal, and, similarly, a second mobile terminal could be termed a first mobile terminal without departing from the teachings of the disclosure.

As will be appreciated by one of skill in the art, the present invention may be embodied as methods, devices, and/or computer program products. Accordingly, the present invention may be embodied in hardware and/or in software (including firmware, resident software, micro-code, etc.). Computer program code for carrying out operations of devices and/or systems discussed herein may be written in a high-level programming language, such as Java, C, and/or C++, for development convenience. In addition, computer program code for carrying out operations of embodiments of the present invention may also be written in other programming languages, such as, but not limited to, interpreted languages. Some modules or routines may be written in assembly language or even micro-code to enhance performance and/or memory usage. It will be further appreciated that the functionality of any or all of the program modules may also be implemented using discrete hardware components, one or more application specific integrated circuits (ASICs), or a programmed digital signal processor or microcontroller. The program code may execute entirely on a single processor and/or across multiple processors, as a stand-alone software package or as part of another software package. The program code may execute entirely on an electronic device or only partly on the electronic device and partly on another device. In the latter scenario, the other device may be connected to the electronic device through a wired and/or wireless local area network (LAN) and/or wide area network (WAN), or the connection may be made to an external computer (for example, through the Internet using an Internet Service Provider).

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and/or the present specification and will not be interpreted in an idealized or overly formal sense unless expressly so defined herein.

For purposes of illustration, some embodiments of the present invention are described herein in the context of a mobile terminal including an athletic competition application, also referred to herein as a "wireless competition device". As used herein, the term "mobile terminal" or "wireless competition device" may include conventional cell phones, Personal Communications Systems (PCS)/smart phones that may include data processing, voice, video, text message, e-mail and/or Web access capabilities, Personal Digital Assistants (PDA) with wireless communications capabilities, wireless pagers, Blackberry wireless handheld e-mail devices, radios, and/or other portable electronic devices that include a wireless transceiver.

By way of background, some embodiments of the present invention may employ location or positioning techniques having certain characteristics in common with conventional location techniques. For example, location may be estimated by collecting a requisite number of ranging measurements (e.g., a time of arrival (TOA), a time difference of arrival (TDOA), and/or an observed time difference (OTD)), from signals passed between transmitter(s) and receiver(s), wherein either the transmitter(s) or the receiver(s) have known or determinable locations (i.e., positions). Further, each of the collected ranging measurements can generally be converted from a time interval measurement to a corresponding distance measurement, for example, by multiplying by the speed of light or an expected speed of transmission associated with the signal. When the conversion from time to distance has been accomplished, traditional triangulation, or other like mathematical techniques, can be used to determine the positional coordinates of the mobile device, based on the known locations and calculated distances.

For example, known location techniques include uplink signal location, downlink signal location, and Global Positioning System (GPS) based approaches. Other known location techniques include approaches based on the Galileo and/or GLONASS global navigation satellite systems. For "uplink signal" location techniques, the mobile telecommunications network is typically configured to determine where the mobile terminal is located based on ranging measurements associated with one or more uplink signals. These uplink signals are transmitted by the mobile terminal and received by a requisite number of receivers having known locations, such as, for example, cellular telephone base stations (BSs). For the "downlink signal" location techniques, the mobile telecommunications network is typically configured to determine where the mobile terminal is located based on ranging measurements associated with the reception, by the mobile terminal, of downlink signals from a requisite number of transmitters having known locations.

For GPS-based location techniques, GPS receivers collect and analyze ranging measurements from signals transmitted by GPS satellites having known locations. The startup of a GPS receiver typically requires the acquisition of a set of navigational parameters from the navigational data signals of four or more GPS satellites. The positions of the GPS satellites vary with regard to time. Thus, a GPS receiver generally needs to receive an accurate measurement of time from the GPS satellites (or an accurate GPS-related source on the ground) in order to know the positions of the GPS satellites at the time of the ranging measurements. The ranging measurements between the GPS receiver and each of at least four (4) GPS satellites occurs by: 1) finding the starting point on the 1023 chip long Gold code sequence within the signal transmitted by each GPS satellite; 2) finding the start time of a bit edge; and 3) finding the start time of the data message. The "time of flight" for the signal received from each GPS satellite is then converted to distance. The resulting four (4) range measurements allow for a solution to the GPS receiver's position in x, y, and z coordinates and for determination of the unknown time difference between the GPS time and the GPS receiver's independent clock.

Thus, the underlying position determination process in accordance with some embodiments of the present invention generally uses signals received from certain known positions, and determines ranging measurements from a sufficient number of signals to solve for the mobile terminal's location. It is known to include a GPS receiver in a mobile terminal to provide position/location functionality.

Some embodiments of the present invention provide an athletic competition application installed on a mobile terminal to provide a wireless competition device that enables two or more users of GPS (and/or other positioning system)-enabled mobile terminals to compete against each other in an athletic event, even when some of the users are not present in the same location. In particular, each user's wireless competition device is configured to collect other positioning data that indicates a distance traveled by the device in association with performance of the athletic event by its user, and is configured to automatically share the collected positioning data for its user with the other wireless competition devices via one or more wireless communication connections. For example, the collected positioning data may indicate and/or may be used to determine a distance traveled by a device over a period of time, an average speed of travel, and/or other athletic performance data. Other data, such as the user's heart rate at particular distances and/or times, may also be collected and shared with the other wireless competition devices. Accordingly, friends who run together every morning can continue to do so even if one is on vacation or out of town on a business trip. Also, the collected positioning data may be stored in the wireless competition device and/or on an external server for use at a later time, for example, so that a user who is sick on the scheduled day for an event can later compete with a friend who completes the event at the scheduled day/time. Moreover, a user of a wireless competition device in accordance with some embodiments of the present invention may establish a wireless connection with a server to initiate, join, and/or search for open athletic events and/or potential competitors without geographic constraints, allowing for competition with others around the world.

Figure 1:
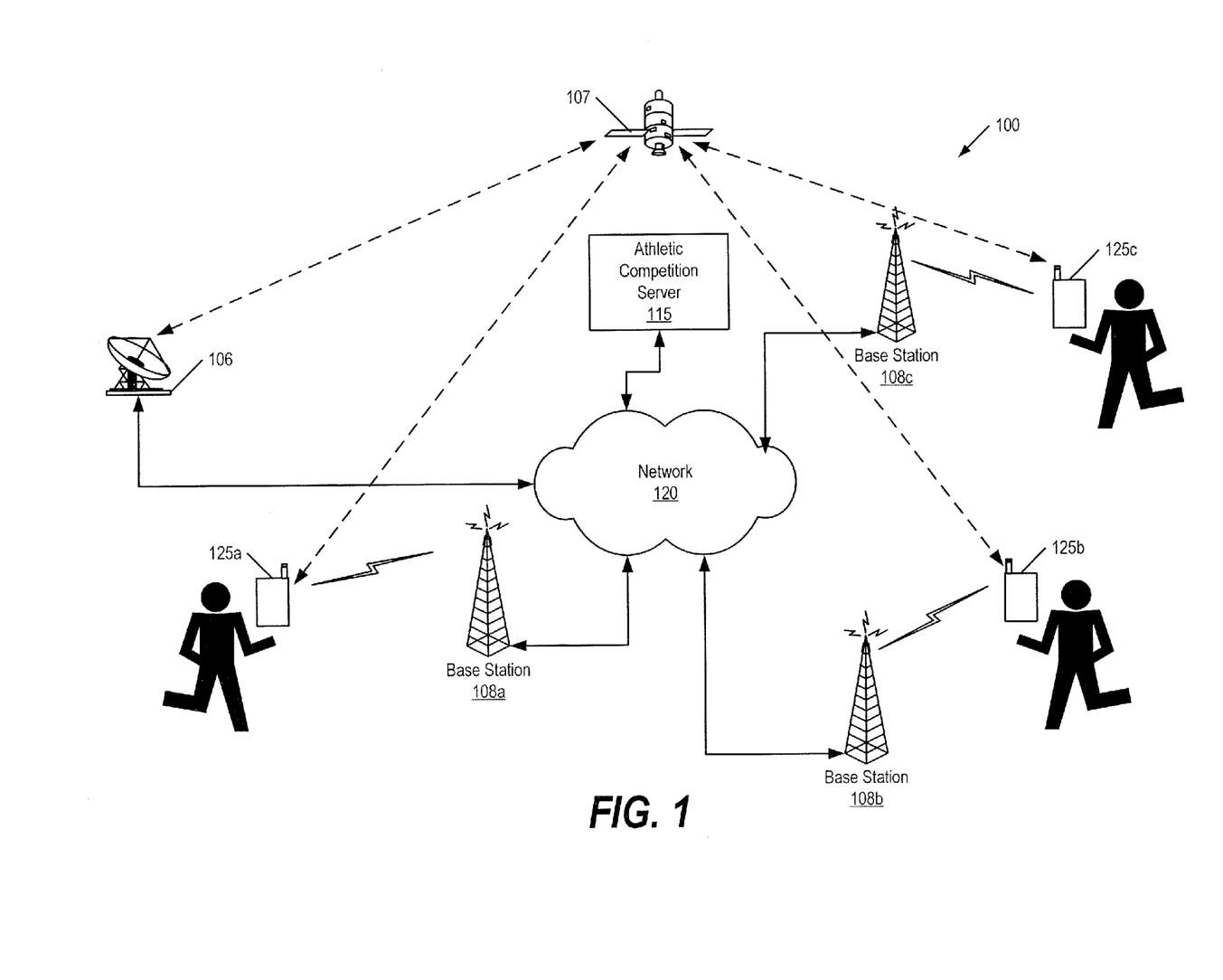
FIG. 1 is a block diagram illustrating a system for participating in an athletic event with a remotely-located competitor using first and second wireless competition devices according to some embodiments of the present invention.

FIG. 1 illustrates a system for participating in an athletic event with one or more remotely-located competitors and related devices and methods according to some embodiments of the present invention. Referring now to FIG. 1, the system 100 provides for remote participation in distance-related athletic events (such as running, bicycling, skating, and/or skiing) by communication of positioning data between a plurality of wireless competition devices 125*a*-125*c*. For example, one or more of the wireless competition devices 125*a*-125*c* may be a cellular telephone, a personal digital assistant (PDA), and/or a dedicated personal training device that is configured to receive and/or store positioning information from which athletic performance data can be derived. It is to be understood, however, that the wireless competition devices 125*a*-125*c* need not all be identical devices. Each of the wireless competition devices 125*a*-125*c* may be located in different geographic locations, and may be configured to communicate over a network 120 via base stations 108*a*-108*c*. The wireless competition devices 125*a*-125*c* may include a wireless local area network (WLAN) transceiver and/or a Public Land Mobile Network (PLMN) transceiver. The system 100 may further include an athletic competition server 115 configured to store and/or distribute positioning data received from one or more of the wireless competition devices 125*a*-125*c* to coordinate and/or facilitate scheduling and/or participation in an athletic event.

The network 120 may represent a global network, such as the Internet, or other publicly accessible network. The network 120 may also, however, represent a wide area network, a local area network, an Intranet, or other private network, which may not be accessible by the general public. Furthermore, the network 120 may represent a combination of one or more wired and/or wireless public and/or private networks and/or virtual private networks (VPN). The network 120 may utilize multiple wireless and/or wireline access protocols. For example, the wireless access protocols may include GSM GPRS, GSM EDGE, GSM UMTS, CDMA 1xRTT, CDMA EVDO, Wi-Fi, and/or Wi-MAX. The wireline access protocols may include, for example, DSL, cable modem, and/or Ethernet.

Still referring to FIG. 1, the wireless competition devices 125*a*-125*c* are configured to establish respective wireless connections with each other and communicate respective positioning data over the wireless communication connections to participate in an athletic event with a remotely-located competitor. The wireless competition devices 125*a*-125*c* may be configured to determine and collect the positioning data corresponding to their current locations using a variety of location calculation techniques, as are well-known in the art. The positioning data may include location, speed, direction, elevation, distance traveled, and/or other data known to indicate the position of a device. For example, in some embodiments, one or more of the wireless competition devices 125a-125c may be configured to communicate its current position, a calculation of distance traveled, and/or its current speed. This way, if one of the wireless competition devices 125a-125c moves into an area that is out of network coverage, the device can continue to calculate its distance traveled. When it returns into area of network coverage, the device can then transmit the data to the other devices, as well as a positioning "plot", for instance, when a user is sick. Also, other devices can use a last-received current speed to make a reasonable estimation of the distance traveled by a device that has moved beyond network coverage. For instance one or more of the other devices may estimate the position and/or distance traveled based on last received speed and direction data, together with known map data. Such estimates could be indicated as such on the respective displays of the other devices.

In some embodiments, the wireless competition devices 125a-125c may be configured to receive GPS communication signals from one or more GPS satellites 107 and/or receivers 106. As such, the wireless competition devices 125a-125c may respectively calculate ranging measurements based on the GPS communication signals and determine the positioning information based on the ranging measurements. More particularly, for each of the wireless competition devices 125a-125c, the ranging measurements for each of at least four GPS satellites may be calculated based on the "time of flight" for the respective communication signals received from each GPS satellite, which may then be converted to distance. The resulting four range measurements allow for calculation of the respective positions of the wireless competition devices 125a-125c, and for determination of the unknown time difference between the GPS time and the independent clocks of the wireless competition devices 125a-125c.

In addition, some or all of the base stations 108a-108c may be configured to provide range assistance information (such as location and/or time correction data) and/or identifiable signals (respectively identifying a signal as transmitted from one of the base stations 108a-108c) in broadcast media content signals, as discussed in U.S. patent application Ser. No. 11/168,044. A range of the wireless competition devices 125a-125c from one or more of the base stations 108a-108c may then determined based on the received identifiable signal and/or the range assistance information, and the position of the wireless competition devices 125a-125c may be determined using traditional triangulation or other like mathematical techniques based on known location data for each of the base stations 108a-108c and the calculated ranges. Also, a network service provider may determine the location of the wireless competition devices 125a-125c using radiolocation and/or trilateration techniques based on the strength of a wireless signal received at the respective base stations 108a-108c, and may relay this information to the wireless competition devices 125a-125c via the network 120. However, other location determination techniques may also be used. For example, one or more of the wireless competition devices 125a-125c my be configured to determine their respective locations using the Galileo and/or GLONASS systems. Such location techniques are well-known in the art and need not be discussed further herein. Also, the location determination techniques used by the wireless competition devices 125a-125c need not all be identical. As such, the wireless competition device 125a may use GPS, the wireless competition devices 125b may use Galileo, and the wireless competition devices 125c may use GLONASS to determine their respective locations without departing from the teachings of the present invention.

Based on the determined locations, the wireless competition devices 125a-125c may be configured to determine respective distances traveled by each of the wireless competition devices 125a-125c during the performance of an athletic event by the corresponding users of the wireless competition devices 125a-125c. In addition, the wireless competition devices 125a-125c may be configured to determine a level of difficulty for the respective courses traveled by each of the wireless competition devices 125a-125c based on changes in elevation and/or rate of ascent/descent indicated by the positioning data. For example, the positioning data calculated for the wireless competition devices 125a may indicate that the user thereof is running a course having a relatively constant elevation, while the positioning data calculated for the wireless competition device 125b may indicate that the user thereof is running a course having significant changes in elevation (e.g., hills). As such, the wireless competition devices 125a and/or 125b may use the positioning data to determine that the user of the wireless competition device 125a is running a relatively easier course than the user of wireless competition device 125b, and may use this determination to scale the calculation of the relative distance and/or speed traveled by the wireless competition devices 125a and/or 125b accordingly. For instance, the devices 125a and/or 125b may determine a scaling factor for their respective positioning data to be used when calculating athletic performance data for the event. The wireless competition devices 125a-125c may also use the positioning data to determine other athletic performance data for their respective users, such as a user's average speed based on the distance traveled by the wireless competition device and the elapsed time during performance of the athletic event.

The wireless competition devices 125a-125c may thereby communicate the positioning data to each other by establishing respective wireless communication connections with one another. For example, the wireless competition device 125a may establish a wireless communication connection with the wireless competition device 125b in response to receiving a selection of the user associated with the wireless competition device 125b, for example, from a phone book or other database stored in the memory of the wireless competition device 125a. As such, the wireless competition device 125a may transmit its positioning data and/or may receive the positioning data for the wireless competition device 125b via the wireless communication connection. In addition, the wireless competition devices 125a-125c may communicate the determined difficulty level for the respective courses traveled by each of the wireless competition devices 125a-125c during performance of the athletic and/or scaling factors therefor event via the respective wireless communication connections. The wireless competition devices 125a-125c may also transmit messages, such as SMS messages, to each other over the network 120 to schedule a start time for the athletic event.

In some embodiments, the wireless competition devices 125a-125c may provide the positioning data to each other in real-time as the data is collected during the ongoing athletic event. However, in other embodiments, the wireless competition devices 125a-125c may collect and store the positioning data for later transmission to one or more of the other wireless competition devices 125a-125c. In still other embodiments, the wireless competition devices 125a-125e may establish respective wireless client-server connections with the athletic competition server 115, which may forward the respective positioning data to one or more of the other wireless competition devices 125a-125c in real-time and/or store the positioning data for later transmission. The wireless competition devices 125a-125e may each display the received positioning data for the other devices relative to its own positioning data to provide a visual indication of the current status of each of the wireless competition devices 125a-125c in the athletic event.

Moreover, the wireless competition devices 125a-125c may be configured to display "scaled" positions for the wireless competition devices 125a-125c based on the determined difficulty of the courses traveled by each of the wireless competition devices 125a-125c. For instance, using the example provided above, the wireless communication devices 125a and 125b may scale the distance, speed, and/or other athletic performance data determined for the wireless communication device 125a downward to compensate for the higher level of difficulty of the course traveled by the wireless competition device 125b. As such, the wireless communication device 125b may be displayed as "ahead" of the wireless communication device 125a even in a situation where the device 125a has actually traveled a greater distance than the device 125b during performance of the athletic event. Other performance data, such as average speed and/or heart rate, may also be scaled and displayed to compensate for the differences in difficulty of the respective courses traveled by the wireless competition devices 125a-125c. Accordingly, the users of the wireless competition devices 125a-125c may fairly compete in the athletic event even under different geographic conditions.

In addition, the athletic competition server 115 may be involved in scheduling the athletic event and/or establishing the wireless communication connections between the wireless competition devices 125a-125c. In particular, the athletic competition server 115 may include a database of scheduled athletic events and/or competitors signed up for the events, including connection information for the wireless competition devices associated with the competitors. As such, the wireless competition device 125a may first establish a wireless client-server connection with the athletic competition server 115 to search for scheduled athletic events and/or competitors. The server 115 may also facilitate scheduling of the event responsive to receiving a user selection of the competitors associated with the devices 125b and/or 125c from the search results. For example, the server 115 may transmit invitations to the wireless devices 125b and 125c associated with selected competitors specifying a type of athletic event as well as a proposed start time for the event, and may receive replies from the wireless competition devices 125b and 125c indicating whether the competitors associated with the wireless devices 125b and 125c accept or decline the invitations. Accordingly, the wireless competition device 125a may establish one or more wireless communication connection with the wireless competition devices 125b and/or 125c at or near the scheduled start time for the athletic event based on the replies received by the server 115. Alternatively, each of the wireless competition devices 125a-125c may establish respective wireless client-server connections with the athletic competition server 115. The athletic competition server 115 may thereby receive and transmit respective positioning data between the wireless competition devices 125a-125c via the respective wireless client-server connections.

Although FIG. 1 illustrates exemplary systems for location-based schedule management using wireless devices according to some embodiments of the present invention, it will be understood that the present invention is not limited to such configurations, but is intended to encompass any configuration capable of carrying out the operations described herein. For example, although described in the preceding example with reference to athletic competition applications executing on the wireless competition devices 125a-125c, it is to be understood that in some embodiments of the present invention, some or all of the functionality described above with reference to the wireless competition devices 125a-125c may be implemented by a server, such as the athletic competition server 115. For example, the athletic competition server 115 may be configured to receive and forward performance data between one or more of the wireless competition devices 125a-125e and/or may transmit/receive messages to/from the wireless competition devices 125a-125c to schedule the athletic event. Likewise, some or all of the functionality described above with reference to the athletic competition server 115, may be implemented in one or more of the wireless competition devices 125a-125c. Accordingly, it is to be understood that the functionality of the system 100 illustrated in FIG. 1 may be implemented by one or more of the wireless competition devices 125a-125c, the athletic competition server 115, the network 120, and/or combinations thereof. In other words, although described above with reference to particular devices having particular functionalities, the functionalities of the particular devices of the system 100 of FIG. 1 may depend on the configuration of the system for participating in an athletic event using wireless competition devices according to some embodiments of the present invention.

Figure 2:
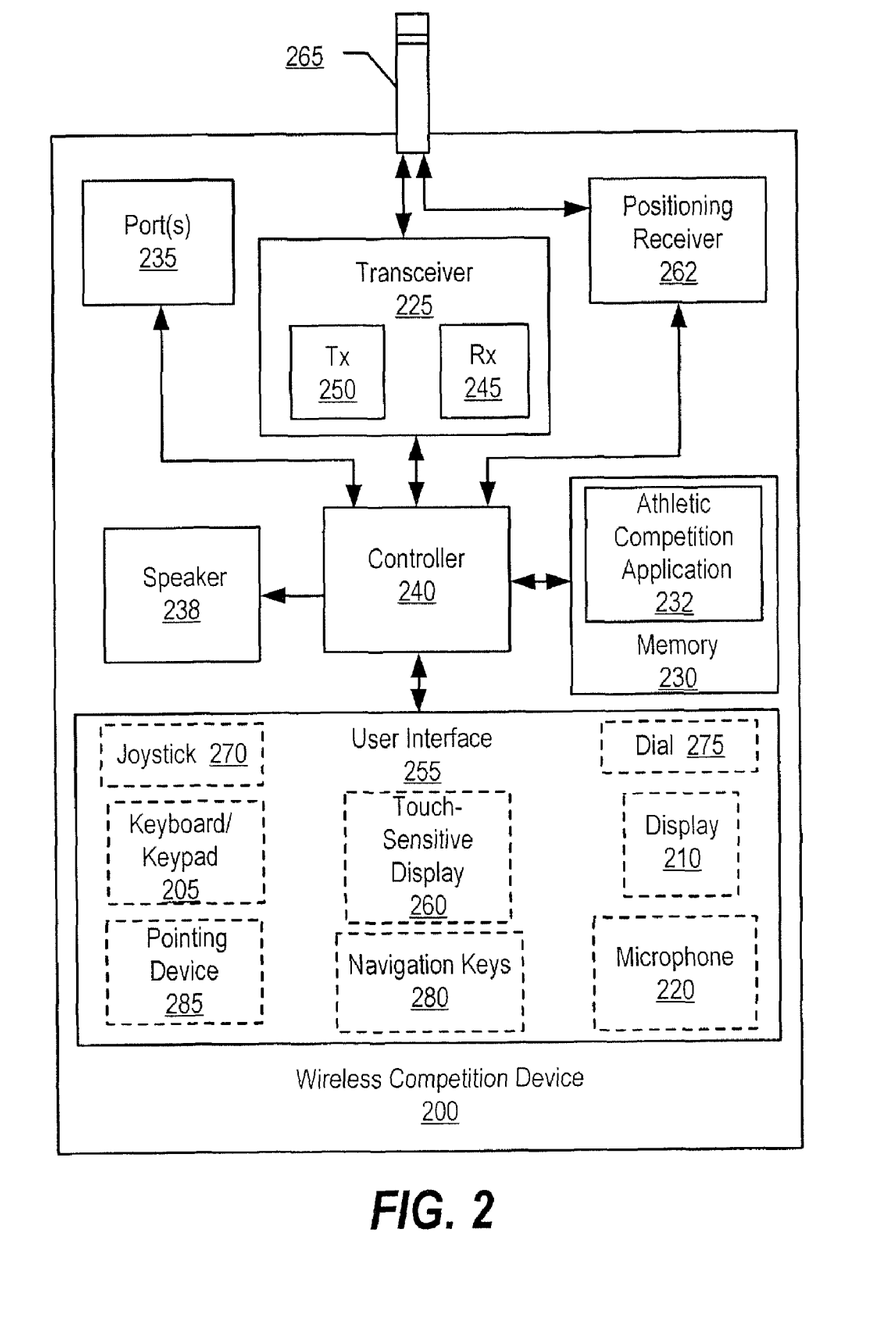
FIG. 2 is a block diagram illustrating a wireless competition device according to some embodiments of the present invention.

FIG. 2 is a block diagram illustrating a wireless competition device 200 according to some embodiments of the present invention. In some embodiments, the wireless competition device 200 may correspond to one of the wireless competition devices 125a-125c of FIG. 1. As shown in FIG. 2, the wireless competition device 200 includes a transceiver 225, an antenna 265, a controller 240, a memory 230, port(s) 235, a speaker 238 and a user interface 255. Depending on the functionalities offered by the wireless competition device 200, the user interface 255 may include a microphone 220, a display 210 (such as a liquid crystal display), a joystick 270, a keypad 205, a touch sensitive display 260, a dial 275, navigation/directional keys 280, and/or a pointing device 285 (such as a mouse, track ball, touch pad, etc.). However, additional and/or fewer elements of the user interface 255 may actually be provided. For example, the touch sensitive display 260 may be provided in a personal digital assistant (PDA) that does not include a display 210, a keypad 205, and/or a pointing device 285.

The transceiver 225 includes a transmitter circuit 250 and a receiver circuit 245, which respectively transmit outgoing radio frequency signals and receive incoming radio frequency signals via an antenna 265. The radio frequency signals may include both traffic and control signals (e.g., paging signals/messages for incoming calls), which may be used to establish and maintain communication with another party or destination. For example, the transceiver 225 may include a public land mobile network (PLMN) transceiver and/or a wireless local area network (WLAN) transceiver. As such, the wireless competition device 200 may use the PLMN transceiver and/or the WLAN transceiver to establish a wireless communication session/connection with a server and/or other electronic device via a base station and/or access point of a wireless network. The wireless data communication connection may be a packet-switched connection, such as that provided by the Enhanced Data GSM Environment (EDGE) standard, the General Packet Radio Service (GPRS) standard, and/or the Universal Mobile Telecommunications System (UMTS) standard, or a circuit-switched connection. In addition, the wireless data communication connection may be established according to a wireless local-area networking standard, such as Wi-Fi and/or Wi-MAX, using the WLAN transceiver. Network security for the wireless local-area network (such as encryption and/or authentication) may be provided according to the applicable network standard being used. While a single antenna 265 is illustrated in FIG. 2 by way of example, separate antennas may be provided for the PLMN transceiver and/or the WLAN transceiver. Alternatively, multiple antennas may be shared by the PLMN transceiver and WLAN transceiver, and/or multiple antennas may be provided for one or both of the PLMN transceiver and WLAN transceiver.

The controller 240 is coupled to the transceiver 225, the memory 230, the speaker 238, and the user interface 255. The controller 240 may be, for example, a commercially available or custom microprocessor configured to coordinate and manage operations of the transceiver 225, the memory 230, the speaker 238, and/or the user interface 255. The memory 230 may represent a hierarchy of memory that may include volatile and/or nonvolatile memory, such as removable flash, magnetic, and/or optical rewritable nonvolatile memory. The foregoing components of the wireless competition device 200 are well-known in the art and need not be described further herein.

As shown in FIG. 2, the wireless competition device 200 also includes a positioning receiver 262. The positioning receiver 262, in cooperation with the controller 240, may provide a processing circuit configured to process ranging signals, for example, as received from GPS satellites. As such, the controller 240 may be configured to determine and/or calculate positioning data indicating changes in the location of the wireless competition device 200 during performance of an athletic event, such as running, bicycling, skating, and skiing, based on the GPS communication signals received via the positioning receiver 262. However, in some embodiments, the controller 240 and/or the positioning receiver 262 may be configured to determine the positioning data for the wireless competition device 200 using other well-known techniques, such as radiolocation and/or trilateration. Also, the positioning receiver 262 may be configured to determine the positioning data based on communication signals received from other positioning systems, such as the Galileo and/or GLONASS satellite navigation systems. The positioning receiver may share the antenna 265 with the transceiver 225 in some embodiments.

Still referring to FIG. 2, the memory 230 includes an athletic competition application 232 that is configured to enable a user of the wireless competition device 200 to participate in an athletic event with one or more remotely-located competitors. In particular, the athletic competition application 232 is configured to receive a user selection of a type of athletic event in which the user wishes to compete and/or one or more desired competitors for the athletic event via the user interface 255. For example, the desired competitor(s) may be selected from a phone book or other database stored in the memory 230 and/or otherwise associated with the wireless competition device 200. The user selection may also include a desired start time and/or a desired distance for the athletic event. The athletic competition application 232 is configured to establish a wireless communication connection with one or more other wireless competition devices associated with the selected competitor(s) and/or event(s), and is configured to receive positioning data for the other wireless competition devices via the transceiver 225. The received positioning data is associated with a past or current performance of the athletic event by a competitor associated with each of the wireless competition devices. The athletic competition application 232 is also configured to transmit the positioning data for the wireless competition device 200 (as calculated based on the signals received via the positioning receiver 262) to one or more of the other wireless competition devices via the transceiver 225. The athletic competition application 232 is configured to display the received positioning data for the wireless competition devices relative to the current positioning data determined by the controller 240 for the wireless competition device 200 in real-time via the displays 210 and/or 260. The athletic competition application 232 may be further configured to scale the received positioning data, for example, based on changes in elevation, rate of ascent/descent, and/or general indications of the difficulty of the courses traveled by the other wireless competition devices, and may display the scaled positioning data for the other devices relative to that of the wireless competition device 200, as discussed above, to compensate for differences in the courses traveled by the competitors in the different locations.

In some embodiments, the athletic competition application 232 may be configured to receive the positioning data from the other wireless competition devices and/or transmit the positioning data for the wireless competition device 200 in real-time. As such, the athletic competition application 232 may be configured to automatically schedule a start time for the athletic event with one or more competitors. For example, the athletic competition application 232 may be configured to transmit an athletic event invitation or challenge to the wireless competition devices associated with one or more selected competitors, and may establish the wireless communication connection(s) prior to the start time of the athletic event responsive to receiving one or more acceptances from the wireless competition devices.

Alternatively, the athletic competition application 232 may establish a wireless client-server connection with a server, such as the athletic competition server 115 of FIG. 1, and may search for open athletic events and/or available competitors. As such, the athletic competition application 232 may present the user of the wireless competition device 200 with a list of the available events and/or competitors from the server, and may establish the wireless communication connection(s) with one or more wireless competition devices responsive to receiving a user selection of available events and/or competitors associated with the wireless competition devices prior to the associated start time(s).

As a further alternative, the athletic competition application 232 may transmit the user selections of the available events and/or competitors to the athletic competition server, which may handle transmitting invitations and/or receiving acceptances from the wireless competition devices associated with the selected events and/or competitors. In addition, the athletic competition application 232 may establish a wireless client-server connection with the server prior to the start time of the scheduled athletic event, and the server may receive and forward the positioning data for the selected wireless competition devices to the athletic competition application 232 in real-time. As such, a single wireless connection with the server may be used to share performance data with multiple competitors. The athletic competition application 232 may also be configured to store the start time, date, and/or other information for the athletic event in a calendar application of the wireless competition device 200, which may be configured to provide an audible, visible, and/or tactile reminder to the user of the wireless competition device 200 via the user interface 255 prior to the scheduled start time of the athletic event.

Although FIG. 2 illustrates an exemplary wireless competition device 200 that may be used to participate in an athletic event with one or more remotely-located competitors according to some embodiments of the present invention, it will be understood that the present invention is not limited to such configuration, but is intended to encompass any configuration capable of carrying out the functionality described herein. For example, as noted above, some of the functionality described above with reference to FIG. 2 may be implemented in a stationary server, such as the athletic competition server 115 of FIG. 1. More generally, while particular functionalities are shown in particular blocks by way of illustration, functionalities of different blocks and/or portions thereof may be combined, divided and/or eliminated.

Figure 3:
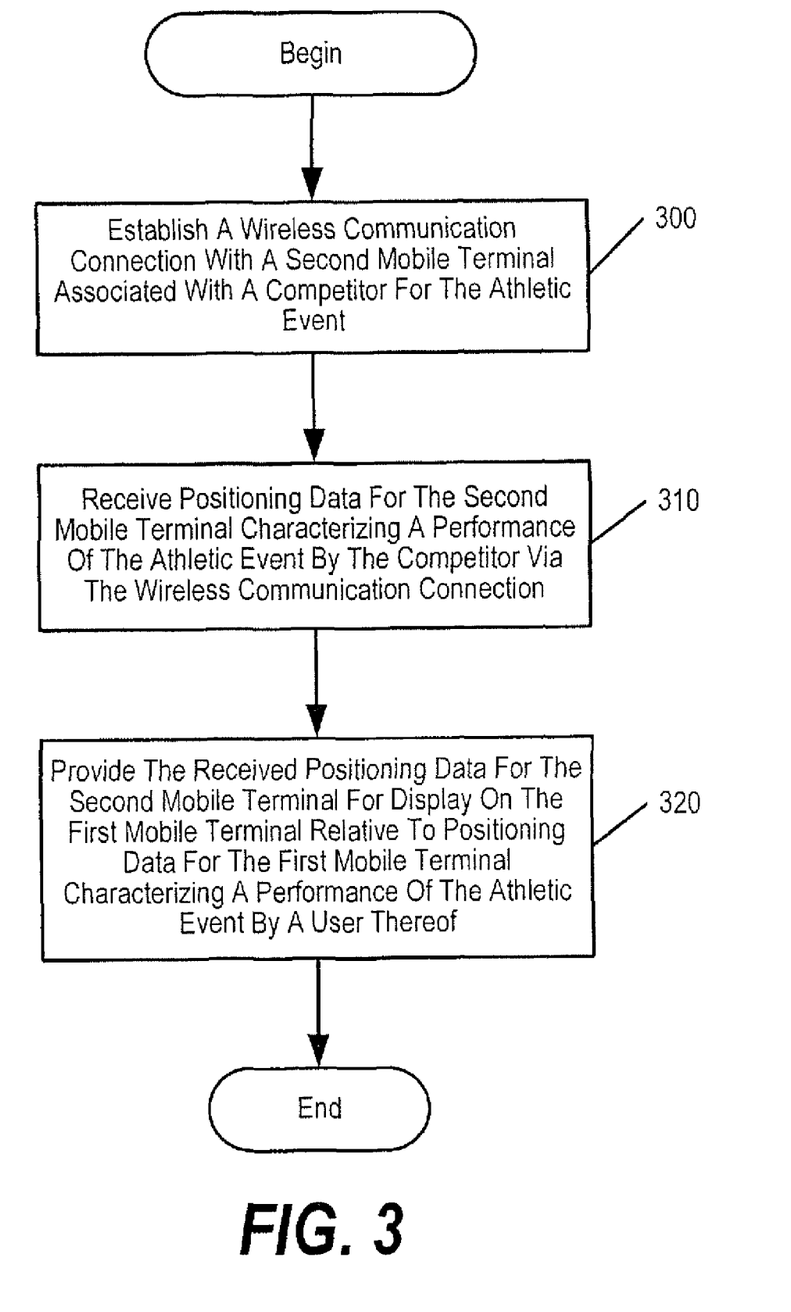
FIGS. 3-5 are flowcharts illustrating example operations for participating in an athletic event with a remotely-located competitor using first and second wireless competition devices according to some embodiments of the present invention.

Example operations for participating in an athletic event with one or more remotely-located competitor in accordance with some embodiments of the present invention will now be described with reference to the flowchart of FIG. 3. In some embodiments, the operations of FIG. 3 may be performed by a mobile terminal, such as the wireless competition device 200 of FIG. 2. However, in other embodiments, the operations of FIG. 3 may be performed by a server and/or other components of a system for remote participation in an athletic event, such as the athletic competition server 115 of FIG. 1. Referring now to FIG. 3, a wireless communication connection is established with a wireless competition device associated with a competitor (hereinafter referred to as a "second" wireless competition device) for the athletic event at Block 300. The wireless communication connection may be established in advance of a scheduled start time for the athletic event. The start time for the athletic event may be set up, for example, by exchanging SMS messages between the second wireless competition device and a first wireless competition device.

At Block 310, positioning data for the second wireless competition device is received via the wireless communication connection. The positioning data is associated with performance of the athletic event by the competitor. The positioning data may include location, speed, direction, elevation, distance traveled, and/or other data known to indicate the position of the second wireless competition device. For example, the positioning data may indicate a distance traveled by the second wireless competition device over a period of time associated with the athletic event and/or an average speed of the second wireless competition device during performance of the athletic event. In some embodiments, the positioning data for the second wireless competition device may indicate a current position of the second wireless competition device, and may be received at Block 310 in real-time to track movement of the second wireless competition device. However, in other embodiments, the positioning data for the second wireless competition device may be a collection of data points representing a prior performance of the athletic event by the associated competitor. The received positioning data for the second wireless competition device is thereby provided for display on the first wireless competition device at Block 320. The received positioning data for the second wireless competition device is provided for display relative to positioning data for the first wireless competition device that indicates performance of the athletic event by a user thereof. Accordingly, a user of the first wireless competition device may view his or her performance of the athletic event relative to that of a remotely-located competitor.

Figure 4:
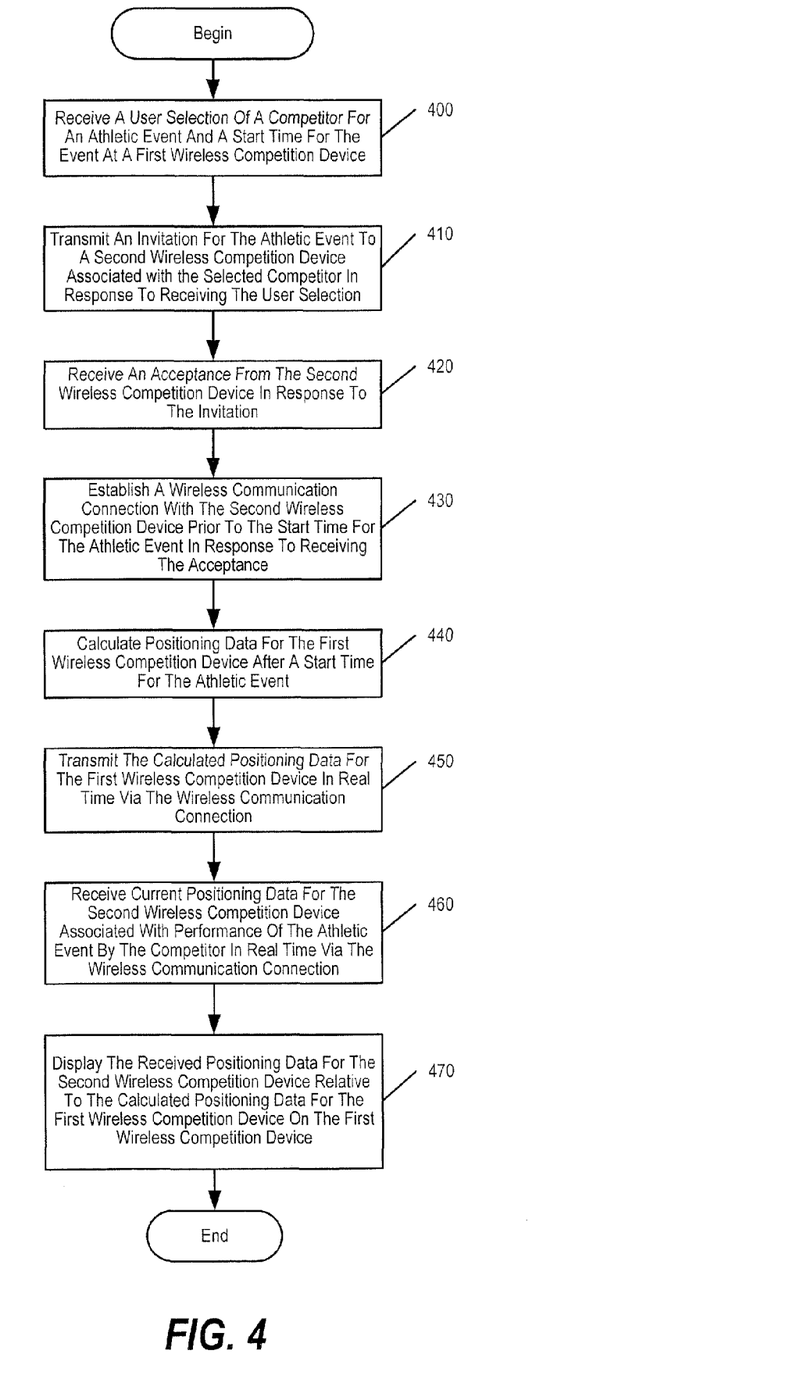

FIG. 4 is a flowchart illustrating more detailed operations for participating in an athletic event with one or more remotely-located competitor in accordance with further embodiments of the present invention. The operations of FIG. 4 may be performed by a mobile terminal, such as one of the wireless competition devices 125a-125c of FIG. 1. Referring now to FIG. 4, a user selection of a desired competitor for an athletic event is received at a first wireless competition device at Block 400. For example, the competitor may be selected from a phone book or other database stored in the first wireless competition device. The user selection may also include a type of athletic event, such as running, bicycling, skating, or skiing, as well as a proposed start time and/or distance for the athletic event. At Block 410, an athletic event invitation or challenge is transmitted to a second wireless competition device associated with the selected competitor in response to receiving the user selection. An acceptance is received from the second wireless competition device at Block 420 in response to the invitation. The invitation and/or acceptance may be communicated between the first and second wireless competition devices by SMS and/or IMS messages in some embodiments. At Block 430, a wireless communication connection is established with the second wireless competition device in response to receiving the acceptance. The wireless communication connection may be established prior to the start time for the athletic event.

Still referring to FIG. 4, after the start time for the athletic event, positioning data is calculated for the first wireless competition device at Block 440 and is transmitted to the second wireless competition device in real-time at Block 450 via the wireless communication connection. For example, the positioning data may be calculated based on GPS signals received by the positioning receiver 262 of FIG. 2. The positioning data for the first wireless competition device is associated with performance of the athletic event by the user of the first wireless competition device. In particular, the positioning data may include data identifying a user (userId), competition (competitionId), counter (packageCounter), relative position (numPositions), current direction (currentDirection), current speed (currentSpeed), and/or distance traveled (distanceCovered). Likewise, positioning data for the second wireless competition device is received in real-time via the wireless communication connection at Block 460. The positioning data for the second wireless competition device is associated with performance of the athletic event by the competitor using the second wireless competition device. Other athletic performance information, such as a heart rate of the user and/or the competitor (currentHeartRate), may also be communicated between the first and second wireless competition devices via the wireless communication connection at Blocks 450 and 460.

At Block 470, the received positioning data for the second wireless competition device is displayed on the first wireless competition device relative to the calculated positioning data for the first wireless competition device. For example, the current distance traveled by the first wireless competition device may be displayed on the first wireless competition device relative to the current distance traveled by the second wireless competition device. The current distances traveled by the first and second wireless competition devices may also be scaled to compensate for the relative difficulty of the respective courses traveled thereby, for example, as determined based on changes in elevation indicated by the respective positioning data. Other athletic performance data, such as the average speed and/or heart rate, may also be displayed at Block 470. For instance, the change of pace required for the first wireless competition device to complete the athletic event before the second wireless competition device may be displayed relative to a current pace of the first wireless competition device. In particular, based on the positioning data for the first and second wireless competition devices, the total distance associated with the athletic event, and the elapsed time, a winner and/or "time to beat" may be projected and displayed. Also, when at least one of the first and/or second wireless competition devices has traveled the total distance associated with the athletic event, at least one of the user and/or the competitor may be displayed as the winner of the athletic event at Block 470.

Figure 5:
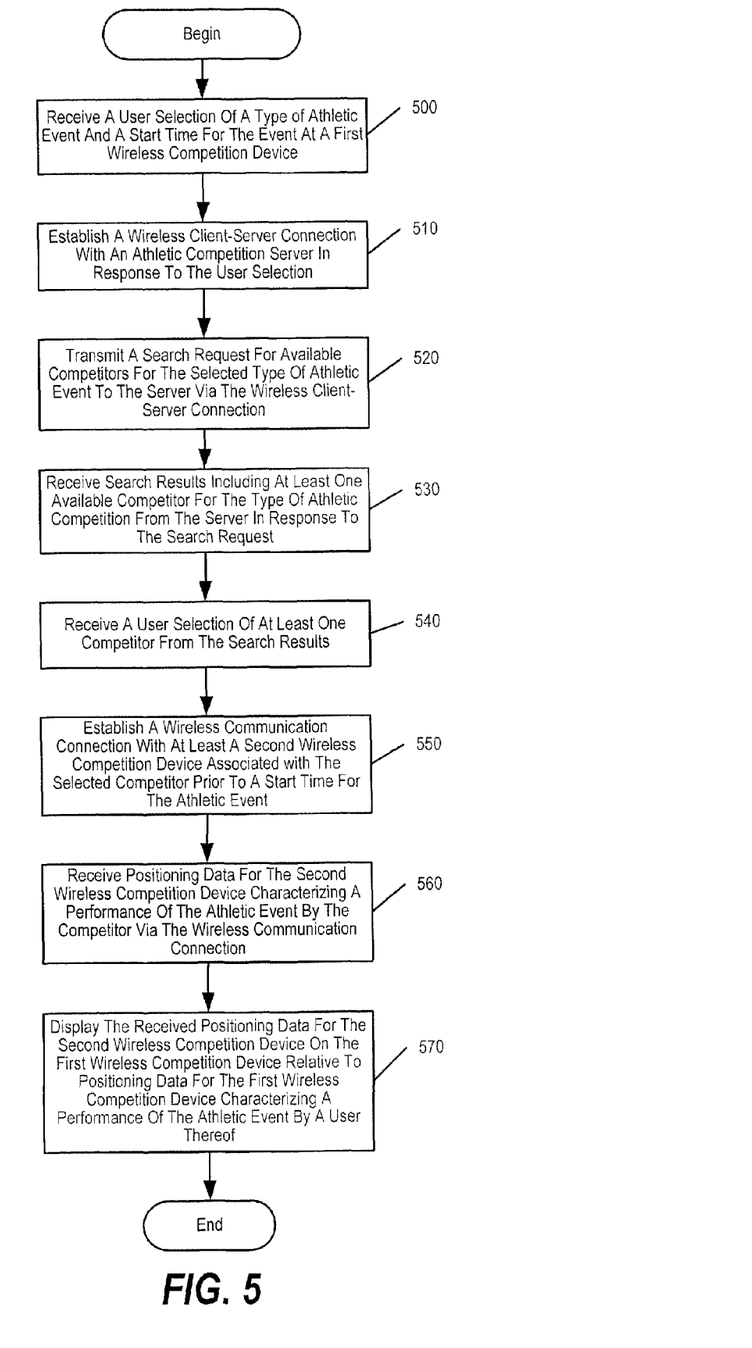

FIG. 5 is a flowchart illustrating detailed operations for participating in an athletic event with one or more remotely-located competitor in accordance with still further embodiments of the present invention. The operations of FIG. 5 may be performed by a mobile terminal, such as one of the wireless competition devices 125a-125c of FIG. 1. Referring now to FIG. 5, a user selection of a type of athletic event in which a user desires to participate is received at a first wireless competition device at Block 500. For example, an athletic competition application program, such as the athletic competition application 232 of FIG. 2, may present a user with a list of athletic event types, and may receive the user selection via a user interface of the first wireless competition device. The types of athletic event may include running, bicycling, skating, skiing, and/or other distance-related athletic events, The user selection may also include a desired start time for the selected athletic event type.

At Block 510, a wireless client-server connection is established between the first wireless competition device and an athletic competition server in response to the user selection. The athletic competition server may include a database of upcoming athletic events and/or competitors signed up for the events. A search request for available competitors for the selected type of athletic event is transmitted to the server via the wireless client-server connection at Block 520, and search results including at least one available competitor for the selected type of athletic event is received from the server via the wireless client-server connection at Block 530. The search results may also include identification and/or connection information for wireless competition devices associated with the competitors, preferred and/or required starting times designated by the competitors for the selected type of athletic event, as well as an indication of a proficiency/skill level for each listed competitor with regard to the selected type of athletic event. At Block 540, a user selection of at least one competitor from the search results is received at the first wireless competition device.

Still referring to FIG. 5, a wireless communication connection with at least a second wireless competition device associated with the selected competitor is established at Block 550 prior to the start time for the athletic event. For example, identification and/or connection information (such as a phone number and/or IP address) for the second wireless competition device may be received from the server in response to the user selection of the competitor associated with the second wireless competition device at Block 540, and the wireless communication connection may be established using the received identification information. Alternatively, a first wireless client-server connection may be established between the first wireless competition device and the athletic competition server, and a second wireless client-server connection may be established between the athletic competition server and the second wireless competition device to provide the wireless communication connection at Block 550. In such embodiments, the athletic competition server need not share the connection information for the wireless competition devices involved in the athletic event, but rather, may receive and transmit positioning data between the first and second wireless competition devices via the respective first and second wireless client-server connections.

At Block 560, positioning data for the second wireless competition device is received via the wireless communication connection. The positioning data is associated with the performance of the athletic event by the selected competitor. At Block 570, the received positioning data for the second wireless competition device is displayed on the first wireless competition device relative to positioning data for the first wireless competition device. The positioning data for the first wireless competition device is associated with performance of the athletic event by the user of the first wireless competition device. Where other competitors are involved in the event, the positioning data for their respective wireless competition devices may also be received via respective wireless communication connections at Block 560 and displayed at Block 570. Accordingly, a user of the first wireless competition device may find and compete with one or more remotely-located competitors via the athletic competition server.

The flowcharts of FIGS. 3 to 5 illustrate the architecture, functionality, and operations of embodiments of hardware and/or software for participation in an athletic event with remotely-located competitors and related devices according to various embodiments of the present invention. It will be understood that each block of the flowchart and/or block diagram illustrations, and combinations of blocks in the flowchart and/or block diagram illustrations, may be implemented by computer program instructions and/or hardware operations. In this regard, each block represents a module, segment, or portion of code, which comprises one or more executable instructions for implementing the specified logical function(s). It should be noted that, in other implementations, the function(s) noted in the blocks may occur out of the order noted in FIGS. 3 to 5. For example, two blocks shown in succession may, in fact, be executed substantially concurrently, or the blocks may sometimes be executed in the reverse order, depending on the functionality involved. These computer program instructions may be provided to a processor of a general purpose computer, a special purpose computer, or other programmable data processing apparatus to produce a machine, such that the instructions, which execute via the processor of the computer or other programmable data processing apparatus, create means for implementing the functions specified in the flowchart and/or block diagram block or blocks.

These computer program instructions may also be stored in a computer usable or computer-readable memory that may direct a computer or other programmable data processing apparatus to function in a particular manner, such that the instructions stored in the computer usable or computer-readable memory produce an article of manufacture including instructions that implement the function specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart and/or block diagram block or blocks.

Further operations for participating in an athletic event with remotely located competitors will now be described in the following examples with reference to the athletic competition application 232 of the wireless competition device 200 of FIG. 2. In particular, the athletic competition application 232 in accordance with some embodiments of the present invention may allow a user of the wireless competition device 200 to 1) challenge a friend or other known competitor to participate in an athletic event; 2) accept an invitation to participate in an athletic event; 3) setup a new athletic event that is open to other competitors; and 4) join a scheduled athletic event.

Challenging a Friend

Some embodiments of the present invention may allow a user of the wireless competition device 200 to challenge a remotely-located friend or other known competitor to participate in an athletic event. In particular, the athletic competition application 232 is configured to receive a user selection of one or more competitors to compete in an athletic event, for example, from a phone book and/or dedicated sports friend list stored in the memory 230 of the wireless competition device 200. As such, the athletic competition application 232 may initiate transmission of an invitation or challenge to the wireless competition device(s) associated with the selected competitor(s) via the transceiver 225. The invitation may include a type of athletic event (such as running, bicycling, skiing, skating etc.), a proposed start time for the event, and/or a distance for the event. The athletic competition application 232 may receive respective messages from the challenged competitors either accepting or declining the invitation. If at least one message indicates that the invitation was accepted, the athletic competition application 232 may be configured to store date and time for the athletic event, for example, in a calendar application of the wireless competition device 200. The calendar application may be configured to provide a reminder to the user of the wireless competition device 200 in advance of the scheduled athletic event. The invitation/acceptance for the athletic event may be communicated between wireless competition devices using SMS and/or IMS messages in some embodiments.

Shortly before the start time for the athletic event, the athletic competition application 232 may be started on the wireless competition device 200 to determine the starting location of the wireless competition device 200 and to establish one or more wireless communication connections with the wireless competition device(s) associated with the selected competitor(s). The athletic competition application 232 may determine the starting location for the wireless competition device 200 based on GPS signals received by the positioning receiver 262, and may establish the wireless communication connection(s) via the transceiver 225. The athletic competition application 200 may further display a countdown until the start time for the athletic event via the display 210 and/or 260.

Accordingly, after the start time for the athletic event, the athletic competition application 232 may, based on the GPS data received by the positioning receiver 262, keep track of the distance traveled by the wireless competition device 200 and exchange the information with the wireless competition device(s) associated with the competitor(s) for the athletic event in real-time as the information is being collected during the ongoing event. The wireless competition application 232 is configured to display information including the current position of the user of the wireless competition device 200 relative to the positions of the competitors, the user's current and/or average speed, the current position and/or speed of the competitors, elevational changes, the user's rate of ascent and/or descent, and also the heart rates of the user and/or the competitors if available. The wireless competition application 232 may also scale the determined performance data for the competitors based on the relative difficulty of the respective courses traveled thereby during the performance of the event, for example, as determined from changes in elevation indicated by the positioning data. When the athletic event is over, the athletic competition application 232 may be configured to display statistics for the user and/or competitor(s) in greater detail, and may prompt the user as to whether to save the data for the completed athletic event in the memory 230 of the wireless competition device 200. The saved data can be further analyzed by the user on the wireless competition device 200 and/or uploaded to a personal computer or other electronic device for further analysis.

Accepting an Invitation

Other embodiments of the present invention may allow a user of the wireless competition device 200 to accept an invitation for an athletic event initiated by a competitor. In particular, the athletic competition application 232 may be configured to receive an invitation to participate in an athletic event from a wireless competition device associated with a competitor, for example, by SMS and/or IMS message. As noted above, the invitation may include a type of athletic event (such as running, bicycling, skiing, skating etc.), a proposed start time for the event, and/or a distance for the event. The athletic competition application 232 may transmit a similar message either accepting or declining the invitation to the wireless competition device associated with the competitor via the transceiver 225 in response to a user selection. If the user selection indicates acceptance of the invitation, the start time, date, and/or other information for the athletic event may be added to a calendar application executing on the wireless competition device 200, which may be configured to provide the user with a reminder or other notification in advance of the start time for the athletic event.

Accordingly, shortly before the start time for the athletic event, the athletic competition application 232 may be launched to determine the starting location for the wireless competition device 200 using the positioning receiver 262 and establish a wireless communication connection with the wireless competition device associated with the competitor who initiated the event via the transceiver 225, as discussed above. The athletic competition application 232 may similarly track the distance traveled by the wireless competition device 200, exchange positioning information with the wireless competition device associated with the competitor, display information regarding the performance of the user of the wireless competition device 200 relative to that of the competitor, etc. as discussed above in the previous example.

Setting Up an Open Athletic Event

Further embodiments of the present invention may allow a user of the wireless competition device 200 to set up an "open" athletic event for participation with one or more remotely-located competitors who may be unknown to the user of the wireless competition device 200. In particular, the athletic competition application 232 may be configured to receive a user proposal to set up an open athletic event. The user proposal may include a type of athletic event (such as running, bicycling, skiing, skating etc.), a start time for the event, and/or a distance for the event. The proposal may also include data indicating the user's skill level and/or previous performance(s) of the selected type of athletic event, for example, so that competitors may select to compete with others having a same skill level. In response to the user's proposal, the athletic competition application 232 may establish a wireless client-server connection with a server, such as the athletic competition server 115 of FIG. 1, and may transmit the proposal for the selected type of athletic event, start time, and/or distance to the server via the wireless client-server connection.

The server may be configured to maintain a database of upcoming athletic events, and may create a new entry for an athletic event according to the received proposal to the database. The server may thereby receive one or more acceptances from wireless competition devices associated with the competitors who wish to compete in the proposed athletic event, and may transmit a message or notification to the wireless competition device 200 indicating the phone numbers and/or IP addresses for the wireless competition devices associated with the competitors who have signed up for the athletic event.

The athletic competition application 232 may be configured to store the start time, date, and/or other information for the athletic event, for example, in a calendar application of the wireless competition device 200, which may be configured to provide the user of the wireless competition device 200 with a reminder in advance of the scheduled athletic event. The athletic competition application 232 may be launched shortly before the start time for the athletic event to determine the starting location for the wireless competition device 200 and establish respective wireless communication connections with the wireless competition devices associated with the competitors for the event, and may track the distance traveled by the wireless competition device 200, exchange positioning information with the competitor's wireless competition devices, display information regarding the performance of the user of the wireless competition device 200 relative to that of the competitors, etc. as discussed above in the previous examples.

Joining a Scheduled Athletic Event

Still further embodiments of the present invention may allow a user of the wireless competition device 200 to search for and/or participate in a previously scheduled athletic event that is "open" to other competitors. In particular, the athletic competition application 232 may be configured to receive a user request to search for an open athletic event. The search request may include the desired type of athletic event, such as running, bicycling, skiing, skating etc. The search request may also include a preferred start time for the event, a preferred distance for the event, and/or a preferred skill level of potential competitors for the event; however, the user may set these and/or other preferences to be ignored in some circumstances so that a sufficient number of search results may be returned. In response to the receiving the search request, the athletic competition application 232 may initiate a wireless client-server connection with a server, such as the athletic competition server 115 of FIG. 1, and may transmit the search request for the selected type of athletic event, start time, distance, and/or competitor skill level to the server via the wireless client-server connection. The server may return search results including one or more athletic events and/or competitors that match the user's search request, and may transmit the search results to the wireless competition device 200 via the wireless client-server connection.

The athletic competition application 232 may receive the search results via the transceiver 225 and display the search results via the display 210 and/or 260 of the wireless competition device 200, and may receive a user selection of one or more of the athletic events and/or competitors from the displayed search results. In some embodiments, the search results may include a phone number and/or an IP address for each listed competitor device for establishing wireless communication connections with the devices. In response to receiving the user selection from the search results, the athletic competition application 232 may store the time(s)/date(s) associated with the user selection in a calendar application to provide a reminder to the user in advance of the selected athletic event(s) as discussed above. Also, as discussed above, the athletic competition application 232 may be launched on the wireless competition device 200 prior to the start time for the event to determine the starting location of the wireless competition device 200 and to establish respective wireless communication connections with the selected competitor(s) and/or the competitor(s) associated with the selected event(s). The athletic competition application 232 may thereby exchange positioning data and/or other athletic performance information with the wireless competition devices associated with the competitors in the athletic event, display positioning information for the wireless competition device 200 relative to the competitor devices in real-time, etc., as discussed above in the previous examples.

In the drawings and specification, there have been disclosed exemplary embodiments of the invention, and although specific terms are used, they are used in a generic and descriptive sense only and not for purposes of limitation, the scope of the invention being defined by the following claims.

That which is claimed:

1. A method of participating in an athletic event with a remotely-located competitor using first and second wireless competition devices, the method comprising:
 establishing a wireless communication connection with the second wireless competition device associated with the competitor for the athletic event;
 receiving positioning data for the second wireless competition device characterizing a performance of the athletic event by the competitor via the wireless communication connection, wherein the received positioning data indicates that a course traveled by the second wireless competition device during the performance of the athletic event by the competitor is located in a different geographic location and includes different geographic conditions than a course traveled by the first wireless competition device during a performance of the athletic event by a user thereof; determining a level of difficulty for the course traveled by the second wireless competition device during the performance of the athletic event based on changes in elevation and/or rate of ascent/descent indicated by the received positioning data; and
 providing the received positioning data for the second wireless competition device for display on the first wireless competition device relative to positioning data for the first wireless competition device characterizing a performance of the athletic event by a user thereof.

2. The method of claim 1, wherein the received positioning data for the second wireless competition device is associated with a previous performance of the athletic event by the competitor, and wherein the positioning data for the first wireless competition device is associated with a current performance of the athletic event by the user.

3. The method of claim 1, wherein receiving the positioning data for the second wireless competition device comprises:
 receiving current positioning data for the second wireless competition device via the wireless communication connection in real-time during the athletic event.

4. The method of claim 3, further comprising:
 transmitting current positioning data for the first wireless competition device to the second wireless competition device via the wireless communication connection in real-time during the athletic event.

5. The method of claim 3, further comprising:
 receiving a user selection of a type of athletic event and/or the competitor for the athletic event; and
 automatically scheduling the athletic event with the competitor responsive to receiving the user selection.

6. The method of claim 5, wherein automatically scheduling the athletic event comprises:

transmitting an invitation for the athletic event to the second wireless competition device in response to receiving the user selection of the competitor; and
receiving an acceptance from the second wireless competition device in response to the invitation,
wherein establishing the wireless communication connection comprises establishing the wireless communication connection with the second wireless competition device prior to a start time for the athletic event in response to receiving the acceptance.

7. The method of claim 6, wherein automatically scheduling the athletic event further comprises:
storing the start time for the athletic event in a calendar application of the first wireless competition device; and
providing an audible, visible, and/or tactile reminder for the athletic event prior to the start time.

8. The method of claim 5, wherein receiving the user selection of the competitor further comprises receiving a user selection of a plurality of competitors, and further comprising:
establishing respective wireless communication connections with a plurality of wireless competition devices associated with respective ones of the plurality of competitors;
receiving respective positioning data for the plurality of wireless competition devices associated with performance of the athletic event by the respective ones of the plurality of competitors via the respective wireless communication connections; and
displaying, on the first wireless competition device, the respective positioning data for the plurality of wireless competition devices relative to the positioning data for the first wireless competition device.

9. The method of claim 5, wherein automatically scheduling the athletic event comprises:
establishing a wireless client-server connection with an athletic competition server in response to receiving the user selection of the type of athletic event;
transmitting a search request for available competitors for the selected type of athletic event to the athletic competition server via the wireless client-server connection;
receiving search results including the competitor associated with the second wireless competition device from the athletic competition server via the wireless client-server connection in response to the search request;
displaying the search results on the first wireless competition device; and
receiving a user selection of the competitor from the displayed search results;
wherein establishing the wireless communication connection comprises establishing the wireless communication connection with the second wireless competition device prior to a start time for the athletic event in response to receiving the user selection of the competitor from the search results.

10. The method of claim 5, wherein automatically scheduling the athletic event comprises:
receiving a user proposal for the athletic event including a start time and distance for the event;
establishing a wireless client-server connection with an athletic competition server in response to receiving the proposal;
transmitting the proposal to the athletic competition server via the wireless client-server connection; and receiving a notification from the athletic competition server when at least the competitor associated with the second wireless competition device has accepted the proposal,
wherein establishing the wireless communication connection comprises establishing the wireless communication connection with the second wireless competition device prior to the start time for the athletic event in response to receiving the notification from the athletic competition server.

11. The method of claim 1, further comprising:
calculating the positioning data for the first wireless competition device at a current time after a start time for the athletic event;
determining a current distance traveled by the first wireless competition device based on the calculated positioning data for the first wireless competition device at the current time; and
determining a distance traveled by the second wireless competition device over a time period corresponding to a difference between the start time and the current time based on the received positioning data for the second wireless competition device,
wherein providing the received positioning data comprises displaying, on the first wireless competition device, the current distance traveled by the first wireless competition device relative to the distance traveled by the second wireless competition device.

12. The method of claim 11, further comprising:
determining a pace for the first wireless competition device to travel a remaining distance associated with the athletic event before the second wireless competition device based on the positioning data for the first and second wireless competition devices; and
displaying, on the first wireless competition device, the pace relative to a current pace of the first wireless competition device.

13. The method of claim 11, further comprising:
determining that at least one of the first wireless competition device and the second wireless competition device has traveled a distance associated with the athletic event based on the positioning data for the first and second wireless competition devices; and
displaying at least one of the user and the competitor as a winner of the athletic event responsive to determining that the at least one of the first wireless competition device and the second wireless competition device has traveled the distance.

14. The method of claim 1,
wherein providing the received positioning data for display comprises scaling the display of the received positioning data on the first wireless competition device according to the determined level of difficulty.

15. The method of claim 1, wherein establishing the wireless communication connection with the second wireless competition device comprises:
establishing a wireless client-server connection with an athletic competition server that is configured to wirelessly communicate with the second wireless competition device,
wherein receiving the positioning data comprises receiving the positioning for the second wireless competition device from the athletic competition server via the wireless client-server connection, and wherein providing the received positioning data comprises displaying the received positioning data for the second wireless competition device on the first wireless competition device relative to the positioning data for the first wireless competition device.

16. The method of claim 15, wherein the athletic competition server is further configured to wirelessly communicate with a plurality of wireless competition devices associated with respective competitors for the athletic event, and further comprising:
receiving respective positioning data for the plurality of wireless competition devices from the athletic competition server via the wireless client-server connection characterizing respective performances of the athletic event by the respective competitors; and
displaying, on the first wireless competition device, the respective positioning data for the wireless competition devices relative to the positioning data for the first wireless competition device.

17. The method of claim 1, wherein establishing the wireless communication connection comprises:
establishing a first wireless communication connection between the first wireless competition device and an athletic competition server; and
establishing a second wireless communication connection between the second wireless competition device and the athletic competition server,
wherein receiving the positioning data comprises receiving the positioning data from the second wireless competition device via the second wireless communication connection, and wherein providing the received positioning data comprises transmitting the received positioning data for the second wireless competition device to the first wireless competition device via the first wireless communication connection.

18. A first wireless competition device, comprising:
a transceiver configured to establish a wireless communication connection with a second wireless competition device associated with a remotely-located competitor for an athletic event;
a controller coupled to the transceiver and configured to receive positioning data for the second wireless competition device via the wireless communication connection, the received positioning data characterizing a performance of the athletic event by the competitor, and to determine a level of difficulty for a course traveled by the second wireless competition device during the performance of the athletic event based on changes in elevation and/or rate of ascent/descent indicated by the received positioning data; and
a display coupled to the controller and configured to display the received positioning data for the second wireless competition device relative to positioning data for the first wireless competition device characterizing a performance of the athletic event by a user thereof,
wherein the received positioning data indicates that a course traveled by the second wireless competition device during the performance of the athletic event by the competitor is located in a different geographic location and includes different geographic conditions than a course traveled by the first wireless competition device during the performance of the athletic event by the user.

19. The wireless competition device of claim 16, further comprising:
a positioning module coupled to the controller and configured to calculate the positioning data for the first wireless competition device at a current time after a start time for the athletic event,
wherein the controller is configured to determine a current distance traveled by the first wireless competition device based on the calculated positioning data for the first wireless competition device at the current time and determine a distance traveled by the second wireless competition device over a time period corresponding to a difference between the start time and the current time based on the received positioning data for the second wireless competition device, and wherein the display is configured to display the current distance traveled by the first wireless competition device relative to the distance traveled by the second wireless competition device.

20. An athletic competition server, comprising:
a transceiver configured to establish a wireless communication connection with a first wireless competition device associated with a remotely-located competitor for an athletic event; and
a processor coupled to the transceiver and configured to receive positioning data for the first wireless competition device characterizing a performance of the athletic event by the competitor via the wireless communication connection, and to determine a level of difficulty for a course traveled by the first wireless competition device during the performance of the athletic event based on changes in elevation and/or rate of ascent/descent indicated by the received positioning data,
wherein the transceiver is configured to provide the received positioning data for the first wireless competition device for display on a second wireless competition device relative to positioning data for the second wireless competition device characterizing a performance of the athletic event by a user thereof,
wherein the received positioning data indicates that a course traveled by the first wireless competition device during the performance of the athletic event by the competitor is located in a different geographic location and includes different geographic conditions than a course traveled by the second wireless competition device during the performance of the athletic event by the user.

* * * * *

UNITED STATES PATENT AND TRADEMARK OFFICE
CERTIFICATE OF CORRECTION

| | | |
|---|---|---|
| PATENT NO. | : 8,172,658 B2 | Page 1 of 1 |
| APPLICATION NO. | : 12/126330 | |
| DATED | : May 8, 2012 | |
| INVENTOR(S) | : Svensson | |

It is certified that error appears in the above-identified patent and that said Letters Patent is hereby corrected as shown below:

In the Patent:

Column 10, Line 64: Please correct "devices 125a-125e"
                to read -- devices 125a-125c --

Column 11, Line 3: Please correct "competition devices 125a-125e"
                to read -- competition devices 125a-125c --

Column 12, Line 11: Please correct "125a-125e and/or may"
                to read -- 125a-125c and/or may --

Column 17, Line 18: Please correct "other distance-related athletic events,"
                to read -- other distance-related athletic events. --

Signed and Sealed this
Eighth Day of January, 2013

David J. Kappos
*Director of the United States Patent and Trademark Office*